(12) United States Patent
Prabhakarpandian et al.

(10) Patent No.: US 9,453,252 B2
(45) Date of Patent: *Sep. 27, 2016

(54) MICROFLUIDIC ASSAY IN IDEALIZED MICROVASCULAR NETWORK FOR SELECTION AND OPTIMIZATION OF DRUG DELIVERY VEHICLES TO SIMULATED TUMORS

(71) Applicant: CFD Research Corporation, Huntsville, AL (US)

(72) Inventors: Balabhaskar Prabhakarpandian, Madison, AL (US); Kapil Pant, Huntsville, AL (US); Charles Joseph Garson, Meridianville, AL (US)

(73) Assignee: CFD RESEARCH CORPORATION, Huntsville, AL (US)

( * ) Notice: Subject to any disclaimer, the term of this patent is extended or adjusted under 35 U.S.C. 154(b) by 752 days.

This patent is subject to a terminal disclaimer.

(21) Appl. No.: 13/715,350

(22) Filed: Dec. 14, 2012

(65) Prior Publication Data

US 2013/0101991 A1 Apr. 25, 2013

Related U.S. Application Data

(63) Continuation-in-part of application No. 12/612,573, filed on Nov. 4, 2009, now Pat. No. 8,380,443, and a continuation-in-part of application No. 12/648,296, filed on Dec. 28, 2009, now Pat. No. 8,355,876.

(51) Int. Cl.
*G01N 33/48* (2006.01)
*C12Q 1/02* (2006.01)
*G01N 33/543* (2006.01)
*G01N 33/50* (2006.01)

(52) U.S. Cl.
CPC ............ *C12Q 1/025* (2013.01); *G01N 33/5008* (2013.01); *G01N 33/54366* (2013.01)

(58) Field of Classification Search
CPC ...................................................... C12Q 1/025
USPC .......................................................... 702/19
See application file for complete search history.

(56) References Cited

U.S. PATENT DOCUMENTS

2006/0154361 A1* 7/2006 Wikswo ............ B01L 3/502746
435/289.1

OTHER PUBLICATIONS

Shevkoplyas et al. (Microvascular Research (2003) vol. 65, pp. 132-136).*
Dickerson et al. (Biotechnology and Bioengineering (2001) vol. 73, issue 6, pp. 500-509).*

* cited by examiner

*Primary Examiner* — Jerry Lin
(74) *Attorney, Agent, or Firm* — Maschoff Brennan

(57) ABSTRACT

An apparatus for assaying a tumor drug delivery vehicle and or drug can include an idealized microvascular network (IMN) of one or more interconnected idealized flow channels in fluid communication through a porous wall with a tissue space (e.g., idealized tissue space) containing animal cells and means for quantifying drug delivery through the IMN to the animal cells.

31 Claims, 17 Drawing Sheets

Serial and Parallel Arrangement of Bifurcations and Junctions

Serial and Parallel Arrangement of Bifurcations and Junctions

Serial and Parallel Arrangement of Bifurcations and Junctions

MICROFLUIDIC ASSAY IN IDEALIZED MICROVASCULAR NETWORK FOR SELECTION AND OPTIMIZATION OF DRUG DELIVERY VEHICLES TO SIMULATED TUMORS

CROSS-REFERENCE TO RELATED APPLICATIONS

This patent application is a continuation-in-part of U.S. Ser. No. 12/612,573 filed Nov. 4, 2009 and a continuation-in-part of U.S. Ser. No. 12/648,296 filed Dec. 28, 2009; which patent applications, are incorporated herein by specific reference in their entirety.

STATEMENT REGARDING GOVERNMENT SPONSORED RESEARCH

This invention was made with government support under 1R43 CA139841-01 awarded by the National Institutes of Health. The government has certain rights in the invention.

BACKGROUND

Existing in-vitro tumor drug delivery models are often poor predictors of drug delivery to tumors. Simple in-vitro models cannot accurately capture complex phenomenon involved in tumor drug delivery, which are affected by the physico-chemical properties drugs and delivery vehicles and complex tumor microvasculature. Tumor microvasculature is substantially different from that found in normal tissue. For example, interstitial pressures are higher in solid tumors than in normal tissues and tumor microvasculature often has higher vascular permeability than normal microvasculature. Such factors should be accounted for by in-vitro models used to accurately evaluate potential drug delivery vehicles.

SUMMARY

The present invention provides methods and apparatus for screening tumor drug delivery vehicles that accounts for the geometric and flow properties, increased permeability, and higher interstitial pressures of tumor microvasculature. The apparatus includes a microfluidic device comprising an optically clear microfluidic chip containing a microvascular network of interconnected flow channels having dimensions from 10-500 µm in cross-section. The luminal surfaces of the flow channels are coated with a confluent layer of cultured endothelial cells and mimic physiological microvascular environments. Tumor cells are cultured in extravascular tissue spaces surrounded by the flow channels. The microchannels are separated from the tissue space by pores in the walls of the channels having dimensions in the range of 0.2-5 µm to represent leaky vessels that allow transport of delivery vehicles across vascular walls and into the tissue spaces. Candidate drug delivery vehicles are introduced into and flowed through the flow channels of the device at physiologically realistic flow rates and shear forces. The ability of candidate drug delivery vehicles to reach and/or permeate cultured tumor cells and/or to transfect tumor cells, for example, may be used to select for and/or optimize the performance of the drug delivery vehicle.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
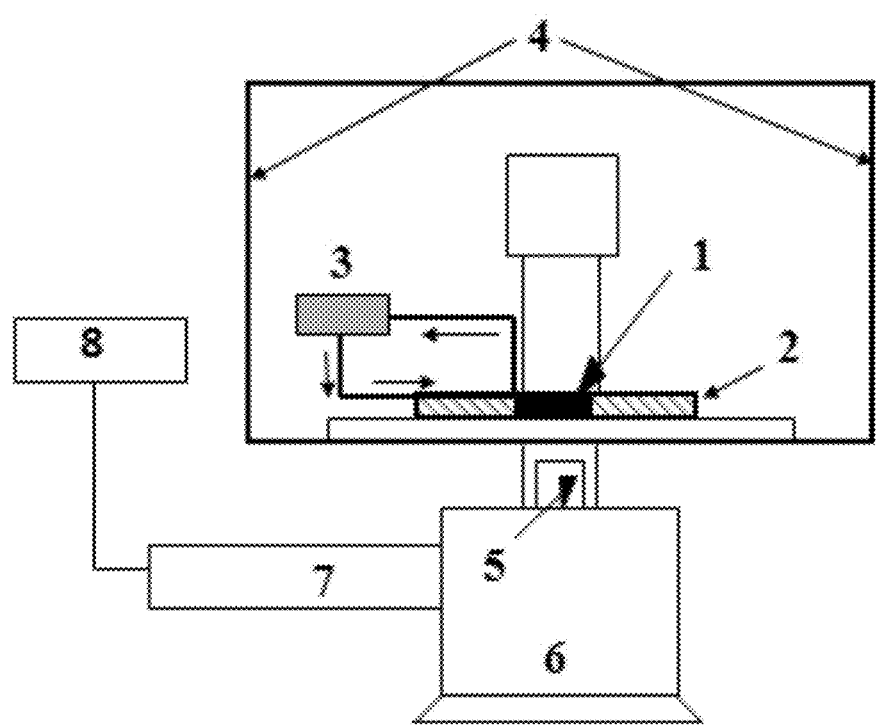
FIG. 1 is a drawing showing the components of a system used for screening tumor drug delivery vehicles.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

A "microfluidic chip" is constructed using well known techniques employed in the semiconductor industry such as photolithography, wet chemical etching, thin film deposition and soft lithography using polymeric substrates, such as Polydimethylsiloxane (PDMS). This is in contrast to microfluidic systems formed in gels made of proteins, chitosan, proteoglycans, and/or other extracellular matrix components. In general, a microfluidic chip is formed with a number of microchannels that are connected to a variety of reservoirs containing fluid materials. The fluid materials are driven or displaced within these microchannels throughout the chip using electrokinetic forces, pumps and/or other driving mechanisms.

A "synthetic microvascular network" (SMN) is a man-made network comprising interconnected, nonlinear flow channels that form geometrical features and have fluid flow properties found in physiological microvascular networks. The flow channels (synthetic vessels) form intersecting networks and may be arranged end to end, analogous to an arteriole, capillary, venuole sequence. Flow channels and the SMNs they form possess geometric characteristics of physiological microvascular including variable cross-sectional shapes, variable cross-sectional areas, convolutions, turns, and/or anastomoses. A network of linear channels joining at angles, for example, is not an SMN because such a network possesses geometrical shapes and produced flow characteristics not found in physiological microvascular networks. Straight channels or other channels having non-physiological geometries may be used to link a synthetic microvascular network to other components of a microfluidic chip. These channels, however, are not a part of the microvascular network. One or more flow channels of a SMN may comprise porous walls such that liquid may move from the interior (lumen) of the flow channel into a space external to the lumen in a manner similar to the movement of fluid from the lumen of a physiological vessel into an interstitial space.

An idealized microvascular network (IMN) is a manmade network comprising interconnected flow channels that have certain fluid flow properties found in physiological microvascular networks. The diameters of the channels range from 10-500 μm and comprise of angles typically between 15° and 135°. One or more flow channels of an IMN may comprise porous walls such that liquid may move from the interior (lumen) of the flow channel into a space external to the lumen in a manner similar to the movement of fluid from the lumen of a physiological vessel into an interstitial space. The pores can be considered to be gaps or apertures that fluidly couple the flow channel and tissue space.

As used herein, the term "idealized" in association with a microfluidic network, junction, or bifurcation is used to describe a synthetic network, junction, or bifurcation consisting of straight microfluidic channels joined at acute, right, or obtuse angles.

As used herein, the word "bifurcation" is meant to include a parent channel splitting into two or more daughter channels. The channels comprising a bifurcation have walls made of a manufactured substrate and may be coated with biological molecules and/or cells. It is further understood that in a general context, a "bifurcation" may also be a junction, which has the same structure as a bifurcation but in which fluid flows in the opposite direction from the daughter channels into the parent channel.

As used herein, a microfluidic channel may have a rectangular, circular, semi-circular, irregular or a combination of cross-sectional shapes. The dimensions of a channel are described, for example, by length, depth and width wherein the depth is measured perpendicular to the plane of a microfluidic chip containing the channel and length and width are measured in directions lying in the plane of the microfluidic chip containing the channel. Channels having circular or semi-circular cross-sections may be described as having variable depth and width relative to channels having rectangular cross-sections or may alternatively be described in terms of channel diameter. Maximum depth and width when used to describe a channel having a circular or semi-circular cross-section are both equal to the maximum diameter of the channel. When used to describe a channel having a rectangular cross-section, the maximum width and depth refer to the constant width and depth of a channel having a constant width and depth or to the highest values for width and depth for channels having variable width and depth.

A microfluidic chip is constructed using techniques employed in the semiconductor industry such as photolithography, wet chemical etching, thin film deposition and soft lithography using polymeric substrates, such as Polydimethylsiloxane (PDMS). Other materials that may be used in place of PDMS include Poly(Styrene Butadiene Styrene) (SBS) and Poly(Styrene-Ethylene-Butadiene-Styrene) (SEBS) elastomers, Polyester-ether (PEE) thermoplast, and thermoset polyester (TPE), which can be used for replica molding fabrication techniques. Polyolefin plastomer (POP's) can be specifically used for submicron range channels. Glass or quartz with reactive wet/dry etching of the microchannels can also be used. Thermoplastic materials such as polymethylmethacrylate (PMMA), polycarbonate (PC), cyclic olefin copolymer (COC), polystyrene (PS), poly vinyl chloride (PVC), and polyethylene terephthalate glycol (PETG) can be used with embossing techniques or injection molding. PS, PC, cellulose acetate, polyethylene terephthalate (PET), PMMA, PETG, PVC, PC, and polyimide can also be used with laser ablation techniques. In general, a microfluidic chip is formed with a number of microchannels that are connected to a variety of reservoirs containing fluid materials. The fluid materials are driven or displaced within these microchannels throughout the chip using electrokinetic forces, pumps and/or other driving mechanisms.

"Tortuosity" is a measure of the indirectness of a vessel or flow channel path. Tortuosity can be measured in several ways. One exemplary means of measuring tortuosity is to sum the angles between consecutive trios of points along the space curve represented by a vessel skeleton and then normalize by path length. Tortuosity may also be measured, for example, by counting inflection points along each vessel or flow channel and multiplying this number (plus one) times the total path length and then dividing by the distance between the ends of the each vessel or flow path.

Tumor cells, as used herein, includes primary and cultured neoplastic cells derived from naturally occurring or artificially induced tumors, as well as normal cells transformed with exogenous nucleic acid to produce neoplastic cell lines. The tumor cells can be immortalized or primary cells. The tumor cells can be obtained from a patient that has cancer, and cultured in the tissue space of the device described herein.

Assay System:

FIG. 1 shows a non-limiting example of a system for performing tumor drug delivery vehicle screening assays according to the present invention. The system comprises a pumping means (3) such as a peristaltic pump (for recirculation/multiple pass) or a syringe pump (single pass) to move fluids through microfluidic channel networks. For experiments with a peristaltic pump, a microfluidic chip (1) is placed on an automated stage device (2) and connected to a pump (3) that is connected to inlets, outlets, and, optionally, ports on the microfluidic chip (1). The microfluidic chip (1) is preferably contained within an incubation chamber (4) and is positioned over an objective lens (5) of a brightfield, phase contrast or fluorescent microscope (6). Optical means such as a CCD camera or video camera (7) are used to visualize cells within the microfluidic chip (1). The camera (7) is in communication with a computer (8) for data collection and control of microscope (6), camera (7), and the microscope mounted accessories. For experiments with a syringe pump, the syringe pump (3) is connected to the microfluidic chip (1) and fluid leaving the microfluidic chip (1) is sent to waste (not shown).

Figure 2:
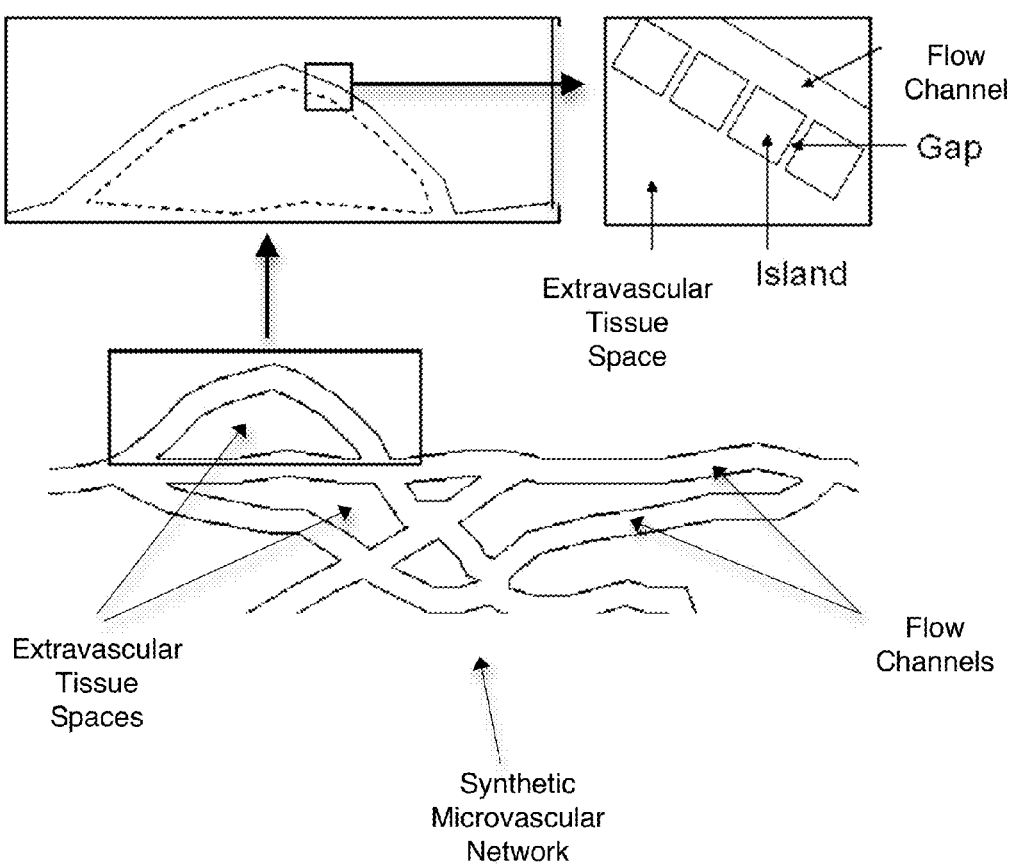
FIG. 2 is a drawing showing a SMN on a microfluidic chip.

Microfluidic Chips:

The microfluidic chips used in the assay system may comprise one or more SMNs, one or more IMNs, or a combination of SMNs and IMNs. FIG. 2 shows several views of a SMN in a microfluidic chip according to the invention. The SMN is made of interconnected nonlinear flow channels that form a geometry that provides physiological flow conditions including convective flow and diffusion. The geometry of the SMN is derived from one or more images of one or more in-vivo microvascular networks. The SMN comprises extravascular tissue spaces separated from the lumen of flow channels by porous walls that allow liquid to diffuse from the flow channels into the tissue spaces. The tissue spaces preferably have cross-sectional luminal dimensions of between 100 µm and 1 cm. In this example, the walls of flow channels surrounding the tissue spaces are constructed with 0.2-5 µm wide gaps to allow liquid diffusion. The portions of the walls of the flow channels between gaps are referred to as islands.

The tissue spaces in a SMN or an IMN preferably comprise a port that serves as an inlet and an outlet for introducing fluid and cells into the tissue spaces and for removing liquid and cells from the tissue spaces. Tissue spaces may also have separate inlets and outlets. The pressure inside each tissue space is preferably regulated through an inlet/outlet port or through a dedicated pressure valve. The walls of at least some of the flow channels that also form the walls of a tissue space are porous to liquids such as aqueous buffers to allow diffusion from the lumen of the microvascular network into the lumen of the tissue space. Porosity may be achieved, for example, by way of gaps, perforations, and/or pores present in the walls of the flow channels. The walls of the flow channels may preferably be coated with a confluent layer of primary or cultured endothelial cells. This may be facilitated by first coating the walls of the flow channels with basement matrix such as Matrigel™, collagen, or other extracellular matrix (ECM) components.

Figure 3:
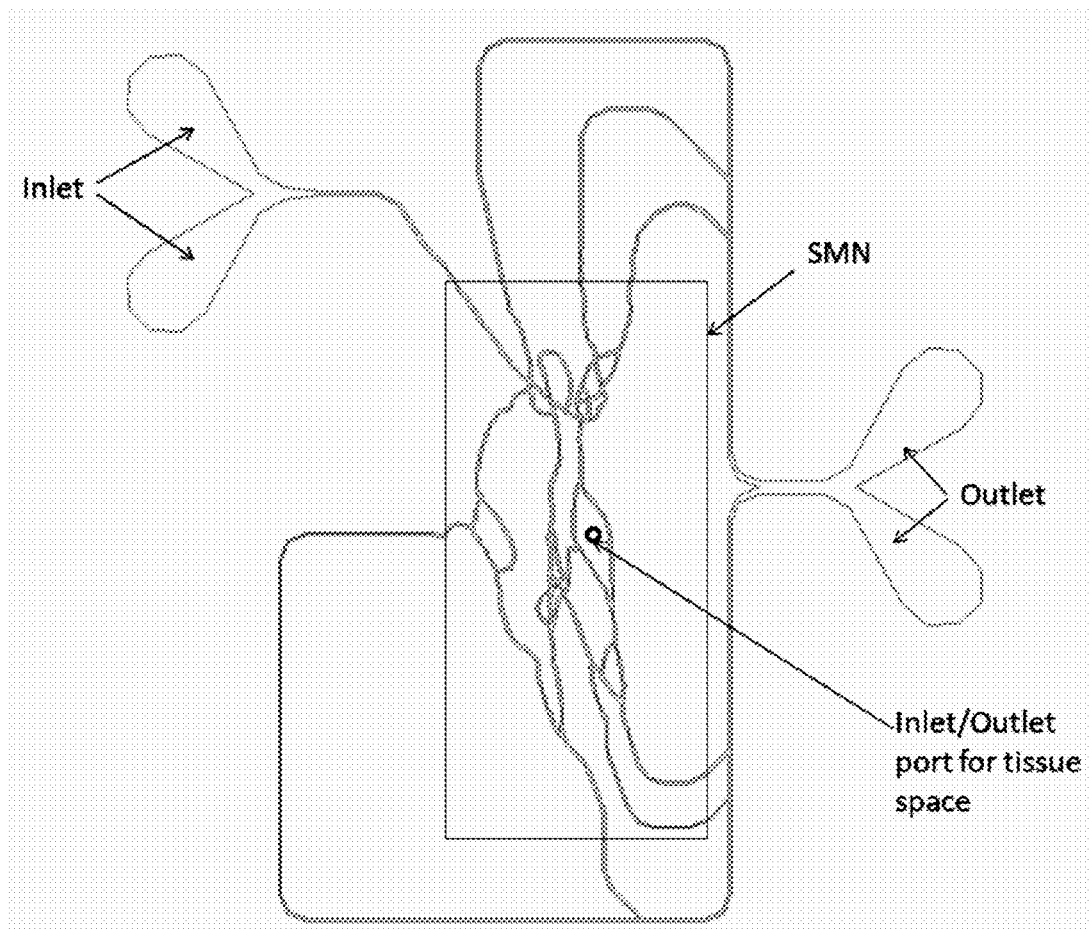
FIG. 3 is a drawing showing the components of a microfluidic chip for screening tumor drug delivery vehicles using a SMN.

FIG. 3 shows an example of a microfluidic chip comprising a SMN. The SMN comprises one or more tissue spaces containing a port that serves as an inlet into and an outlet from the tissue space. The SMN is in fluid communication with an inlet and an outlet via microfluidic channels connected to nonlinear flow channels in the SMN.

Figure 4:
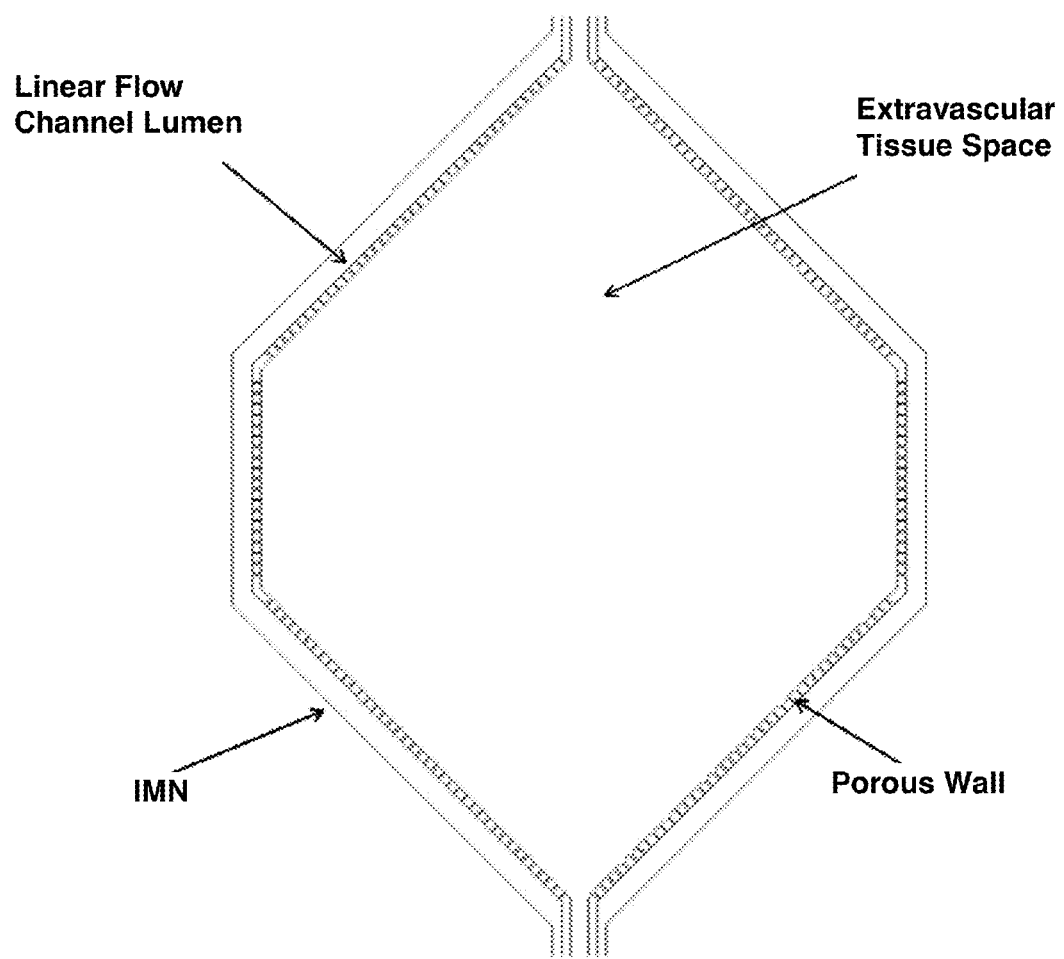
FIG. 4 is a drawing showing an IMN on a microfluidic chip.

FIG. 4 shows a portion of an IMN in a microfluidic chip. In this example, an extravascular tissue space is surrounded by linear flow channels. The walls of the linear flow channels contain gaps, preferably from 0.2 µm to 5 µm wide, or pores, preferably from 0.2 µm to 5 µm in diameter, that allow fluid to diffuse from the flow channels into the tissue space.

Figure 5:
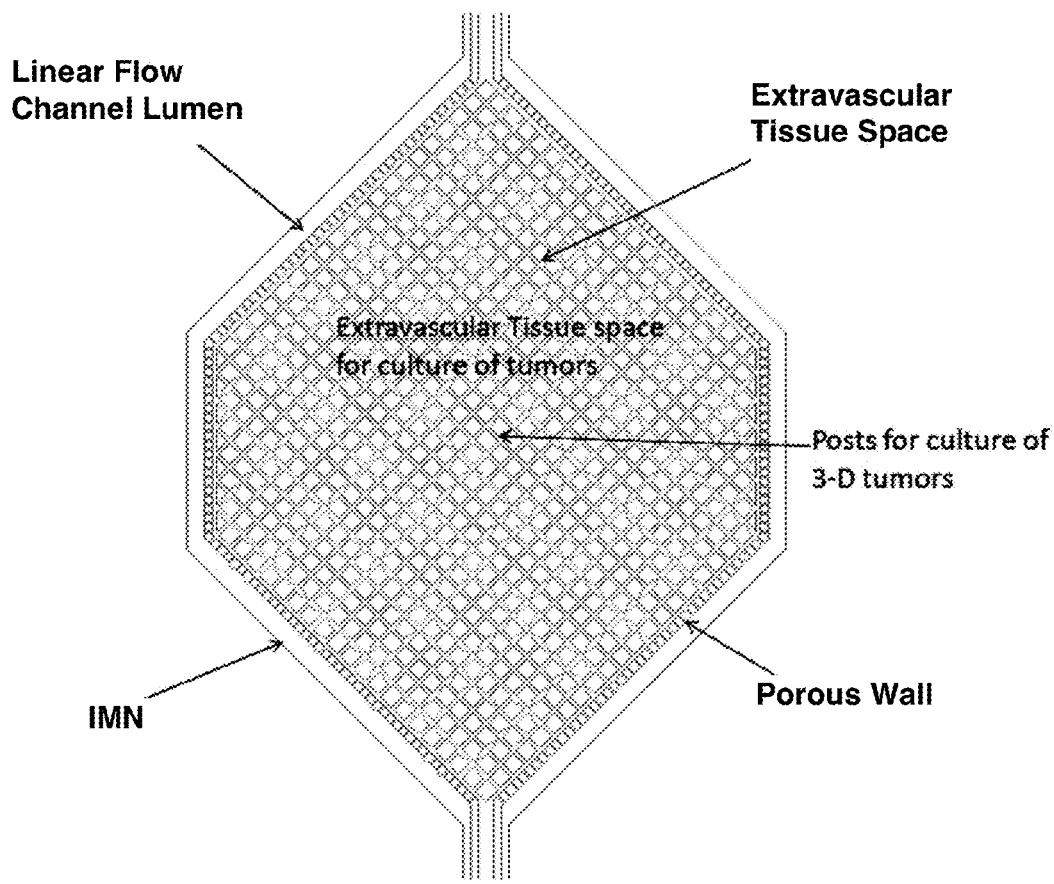
FIG. 5 is a drawing showing an IMN on a microfluidic chip for growing tumor cells to simulate a 3-dimensional solid tumor.

FIG. 5 shows a portion of an IMN comprising an extravascular tissue space that contains posts configured to facilitate the growth of adhesion dependent tumor cells to for a 3-dimensional solid tumor. While the network in this example is an IMN, 3-dimensional solid tumors may be grown in SMNs as well. Although the microfluidic chips and microvascular networks of the invention are largely planar, the depth of tissue spaces and the inclusion and arrangement of posts or other scaffolds within the tissue spaces can be designed to produce tumor cell monolayers and bilayers, as well as 3-dimensional solid tumors. The location of each tissue space in the network may be selected by the user. However, in the case of tumor vasculature derived from images using techniques such as intra-vital microscopy, the locations of tissue spaces are kept the same as observed in-vivo.

Figure 6:
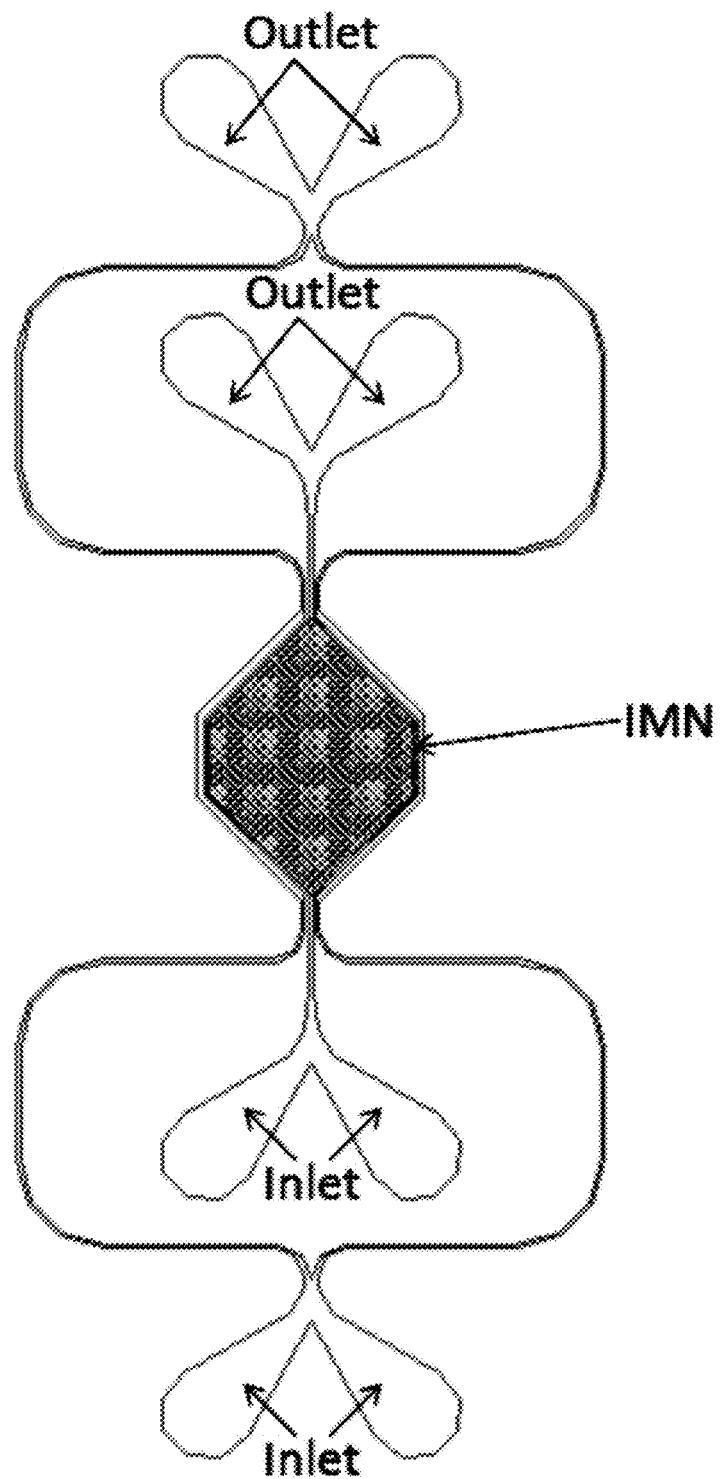
FIG. 6 is a drawing showing the components of a microfluidic chip used for screening tumor drug delivery vehicles using an IMN.
Figure 7:
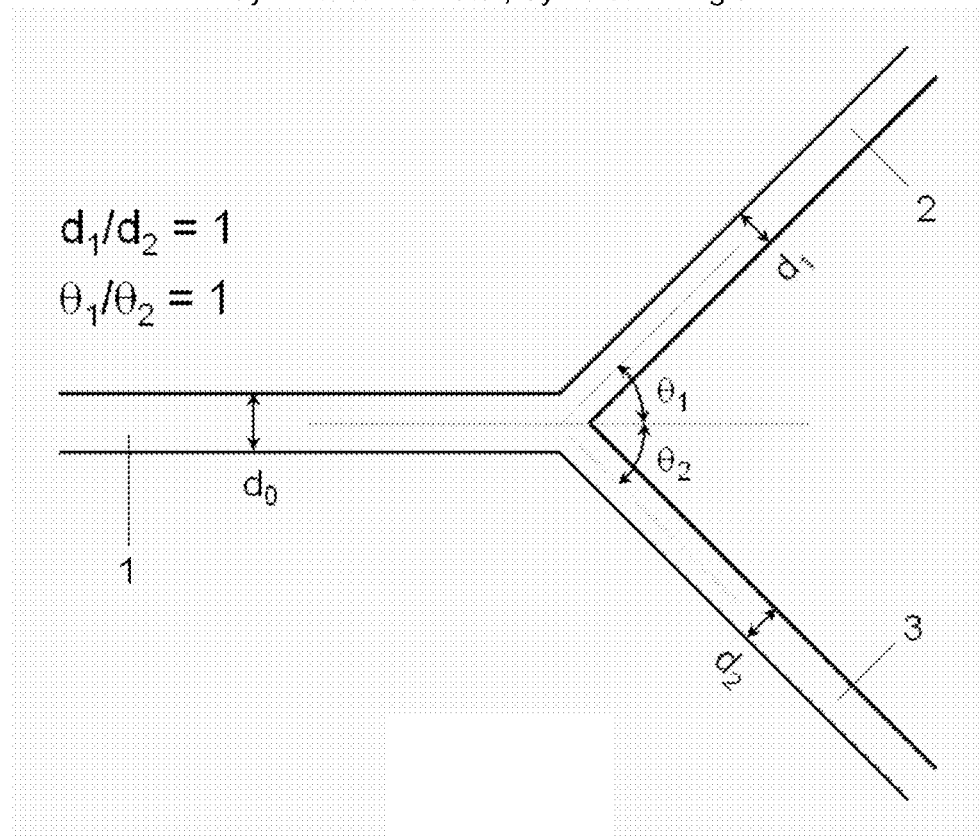
FIG. 7 shows a symmetric bifurcation with symmetric daughter diameters.
Figure 8:
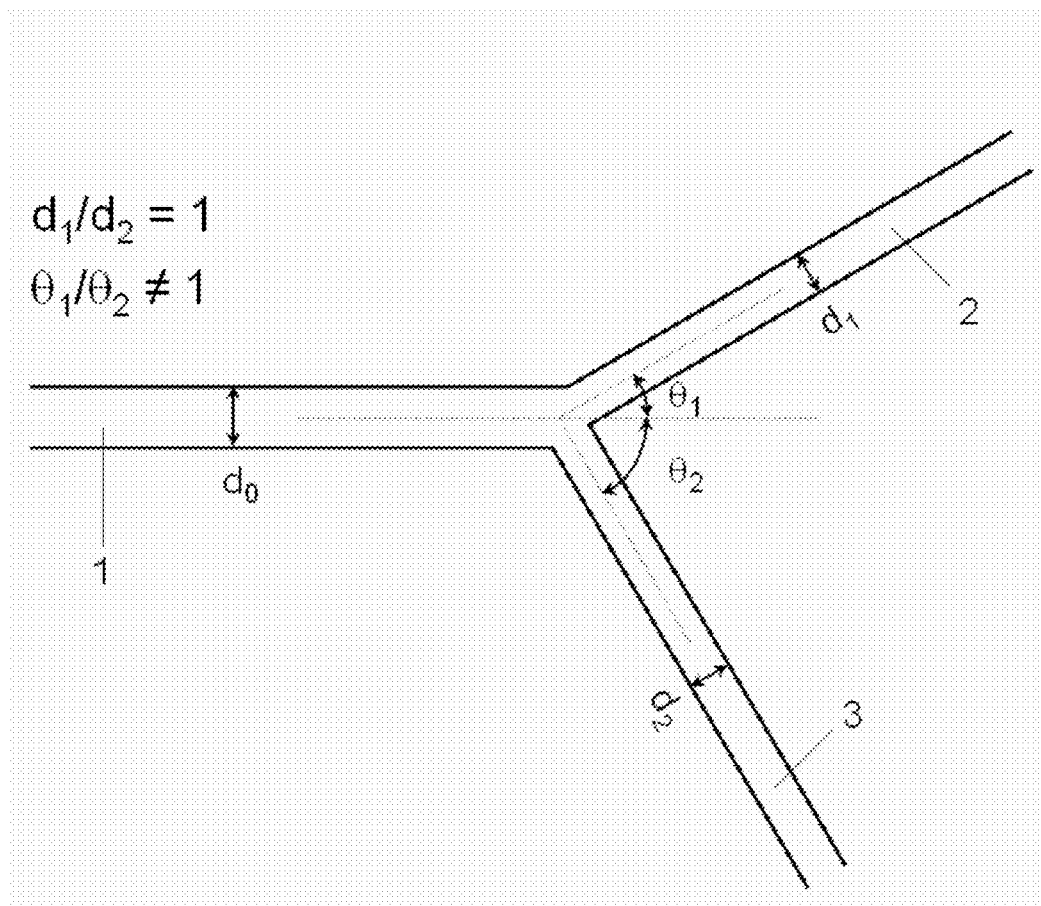
FIG. 8 shows an asymmetric bifurcation with symmetric daughter diameters.
Figure 9:
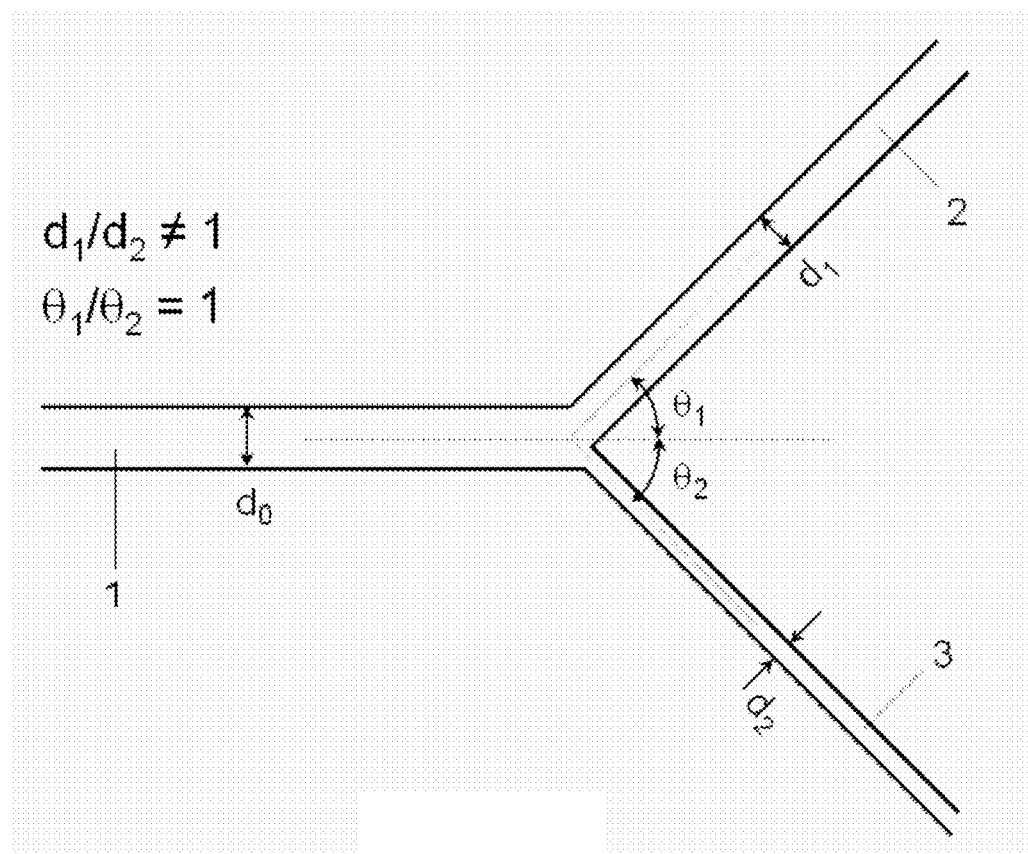
FIG. 9 shows a symmetric bifurcation with asymmetric daughter diameters.
Figure 10:
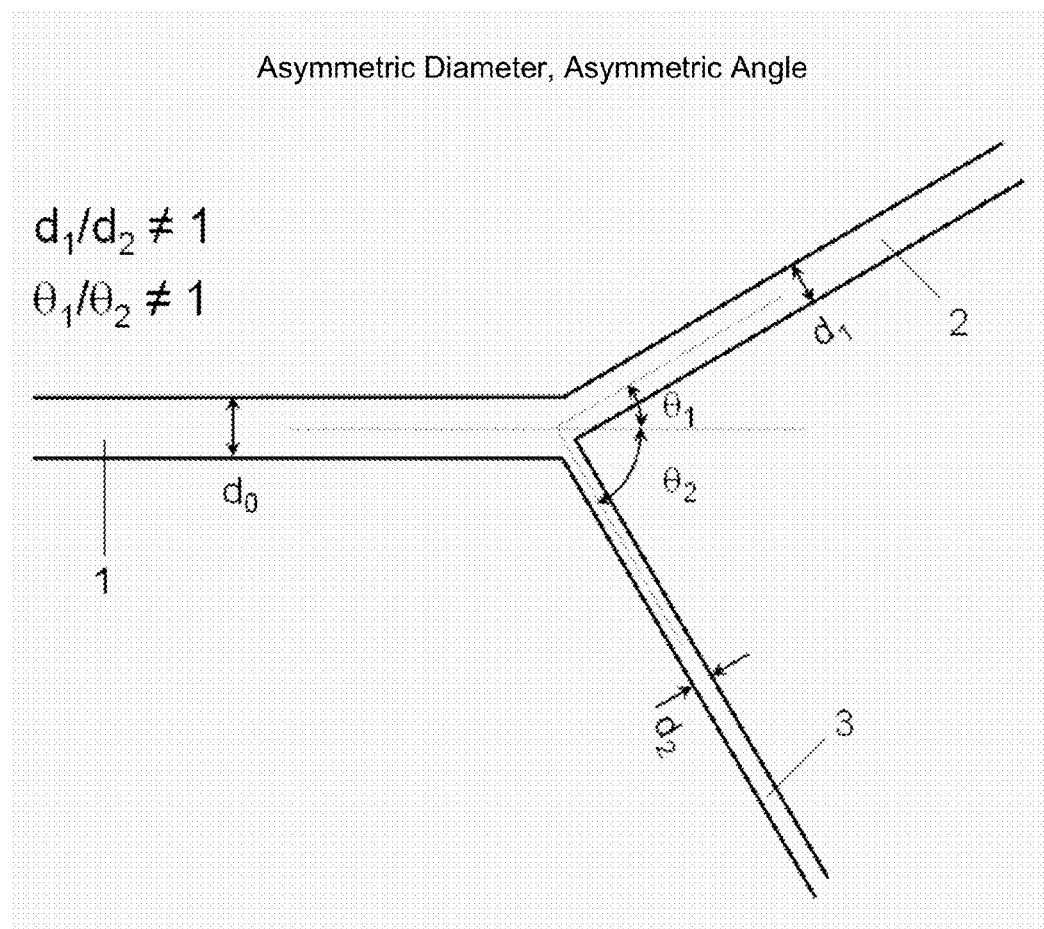
FIG. 10 shows an asymmetric bifurcation with asymmetric daughter diameters.

FIG. 6 shows an example of a microfluidic chip comprising an IMN, with a tissue space containing posts that serves as anchors to facilitate the formation of a 3-dimensional tumor. The posts can include a cross-sectional profile of any shape and appropriate dimension. For example, the posts can be circular, triangular, square, rectangle, pentagon, hexagon, polygon, irregular, or combinations thereof. The posts can have a cross-sectional profile with a dimension from one side to another that ranges from about 5 microns to about 100 microns, or from about 25 microns to about 75 microns, or preferably about 50 microns. The spacing between each posts can also be the same as mentioned above. The IMN and the tissue space are each in fluid communication with a fluid inlet and a fluid outlet. Separate dedicated inlets and outlets for the IMN and the tissue space allow fluid to be pumped through both the IMN and the tissue space. Fluid flows through the inlet and outlet of the IMN can be controlled to maintain specified flow rates and shear rates, for example. Fluid flow and/or pressure applied through the inlet and outlet of the tissue space may be controlled to maintain a simulated interstitial pressure or to simulate lymphatic drainage.

Obtaining Geometries for SMNs:

The geometries for SMNs are derived from physiological microvascular networks. A geometry may, for example, be an exact replica of a digitized image of a natural microvascular network or an average of several digitized images. Maps of complete microvascular networks are constructed from a collage of arterioles, capillaries and venuoles. An entire network is digitized by tracing each vessel on the assembled collage in AutoCad Map™ using a computerized drawing board such as Drawing Board III™, CalComp.

After a network is digitized, an AutoCad Map™ cleanup routine is used to ensure all vessels are properly connected at their common nodes. A tolerance value is set which distinguishes between common nodes and neighboring end points. Each vessel is graphically represented by a polyline consisting of a series of straight lines connected through vertices. The routine compares the distances between successive vertices in a polyline to the set tolerance value. The vertex is removed from the polyline if the distance is below the set tolerance value. Tumor vascular structures can be obtained using intra-vital microscopy techniques and animal models, such as dorsal skin window models and open brain model in rodents. Additional methods of imaging tumor microvasculature include digital photographs of tumor microvascular networks.

Reconstructed "Averaged" Microvascular Networks:

Averaged or nominal microvascular networks are based on the geometries of at least two actual physiological microvascular networks. The images are analyzed as described above and subjected to a detailed morphological analysis to yield statistical data of morphometric parameters such as ratios of parent to daughter vessel diameters, branching angles, distances between branches, rations of branch length to branch channel diameter, tortuosity, bifurcation branch density, and recombining branch density. Averaged microvascular networks can be generated by using averaged morphometric data and/or stochastic sampling of probability density functions for morphometric data. Averaged microvascular networks may be generated using values selected from a variety of statistical distributions for individual morphometric parameters. The values used need not be "average," "mean," or "median" values for measured morphometric parameters.

Idealized Microvascular Networks (IMNs):

Idealized microvascular networks comprise single or multiple bifurcations and/or junctions consisting of linear parent and daughter channels having rectangular or circular or semi-circular cross-sections that diverge or converge at angles of between 15° and 135°. The diameters or cross-sections of the channels are between 10 μm and 500 μm. The bifurcations and junctions are categorized as illustrated in FIG. 7 through FIG. 10. In the figures, $d_0$, $d_1$, and $d_2$ represent the diameters of the parent (1) and first and second daughter channels (2, 3), respectively. $\Theta_1$ and $\Theta_2$ represent the angles formed between the parent channel (1) and the first and second daughter channels (2, 3), respectively. "Diameter" in the context of channels having a rectangular cross-section refers to the longest cross-sectional distance and cross-sectional area is calculated as width×depth. For channels having circular cross-sections, cross-sectional area is calculated as diameter×diameter×π/4. For channels having semi-circular cross-sections, "diameter" refers to the longest cross-sectional dimension and cross-sectional area is calculated as diameter×diameter×π/8.

Figure 12:
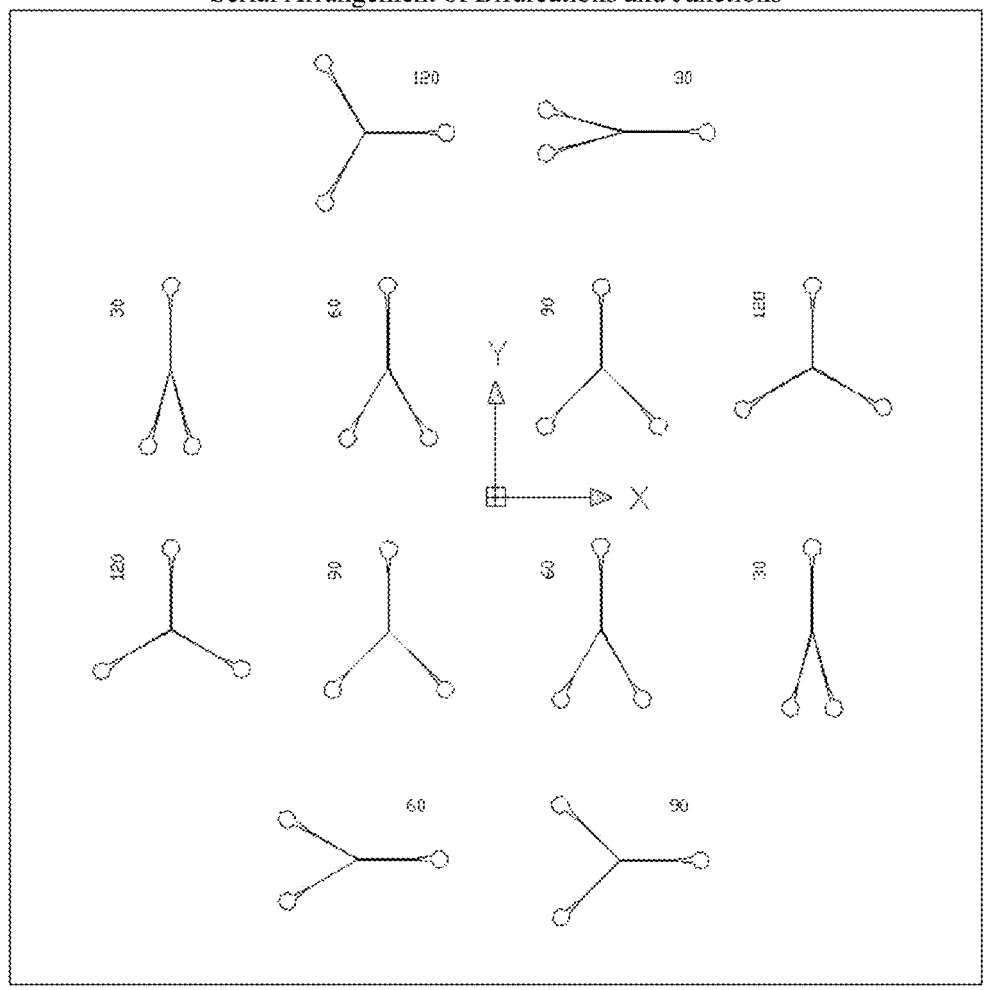
FIG. 12 is a drawing of a microfluidic chip comprising a plurality of symmetric microfluidic bifurcations with 30°, 60°, 90°, and 120° angles configured sequentially for particle and cellular adhesion assays.
Figure 13:
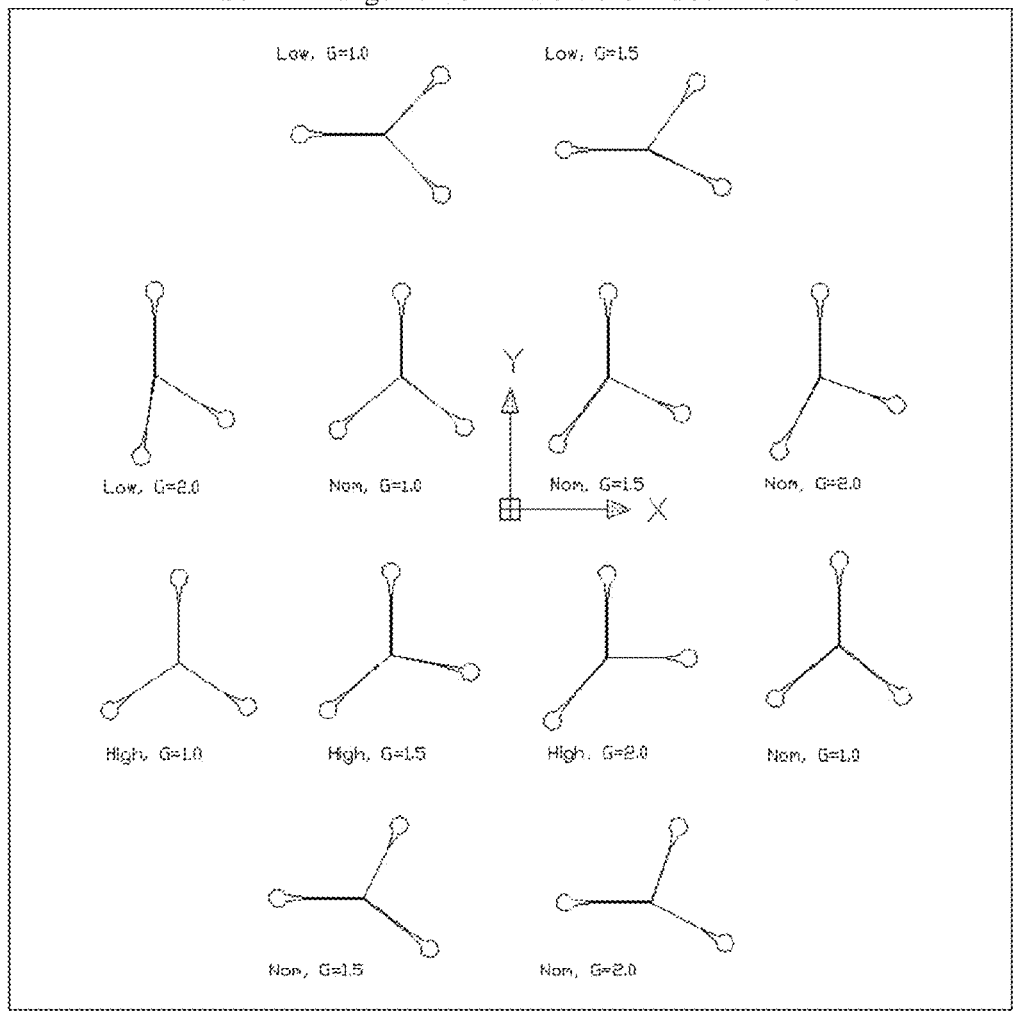
FIG. 13 is a drawing of a microfluidic chip comprising a plurality of asymmetric microfluidic bifurcations with low, nominal, and high contained angles wherein low refers to the smallest contained angle and high refers to the largest contained angle.

The method of the present invention may employ a single idealized bifurcation or junction or, more preferably, the serial or simultaneous use of plurality of junctions and/or bifurcations. FIG. 12 and FIG. 13 illustrate single microfluidic chips, each comprising a plurality of microfluidic bifurcations/junctions arranged for simultaneous use or in a serial fashion, one after another. FIG. 12 shows a microfluidic chip comprising a plurality of symmetric bifurcations with different contained angles (30°, 60°, 90°, and) 120° used sequentially to implement a method of the invention, such as a study on tumors as described herein with IMN devices. FIG. 13 shows a microfluidic chip comprising a plurality of asymmetric bifurcations with Low, Nom, and High contained angles, wherein Low refers to the smallest contained angle, and High refers to the largest contained angle. The degree of angle asymmetry is indicated by G=1, G=1.5, and G=2.0, where increasing G values indicate increasing asymmetry in the bifurcation and the bifurcations are used sequentially to implement a particle and cellular adhesion assay, which can be applied to tumor studies where the particle is a drug delivery vehicle and the cells are cancerous cells such as metastatic cancer cells.

Figure 14:
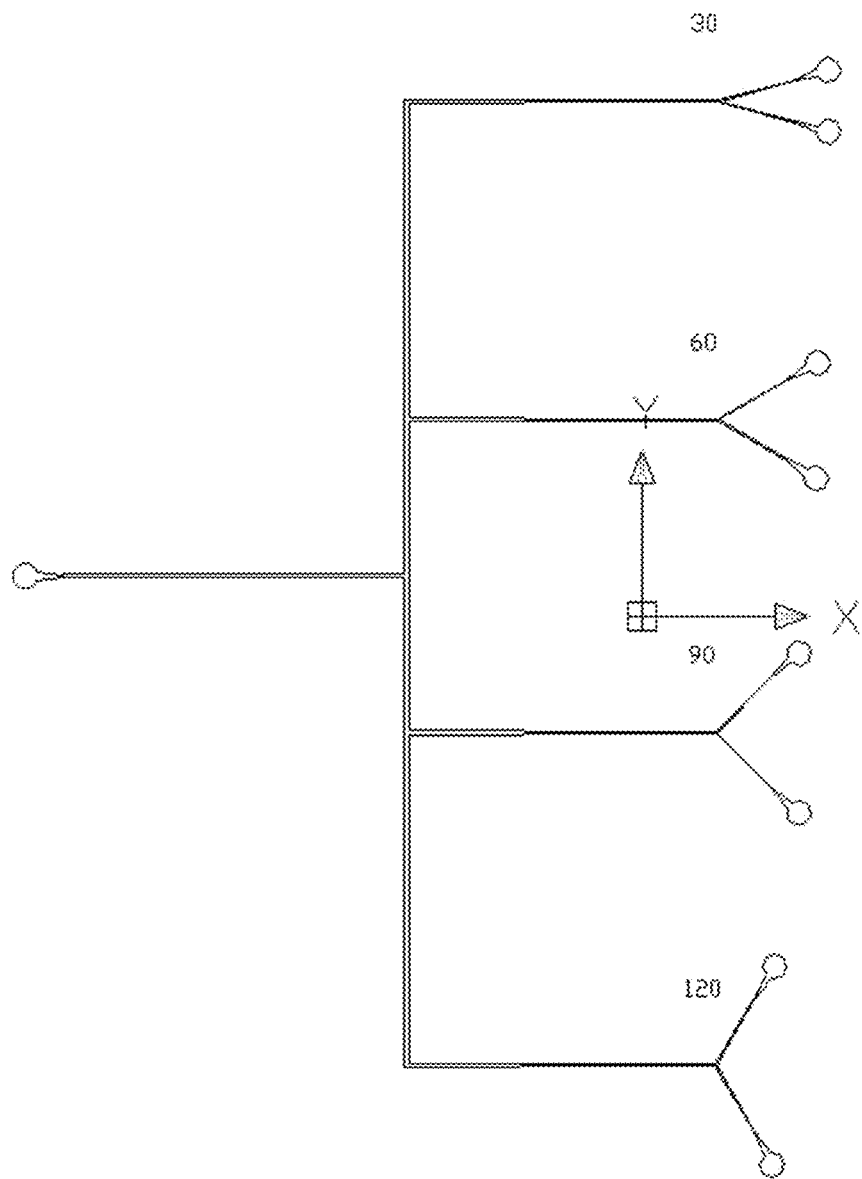
FIG. 14 is a drawing of a single microfluidic chip comprising a plurality of bifurcations arranged in parallel.

The methods of the present invention may also employ a plurality of idealized bifurcations or junctions arranged in parallel or in series. FIG. 14 illustrates a single microfluidic chip comprising a plurality of bifurcations arranged in parallel.

Figure 15:
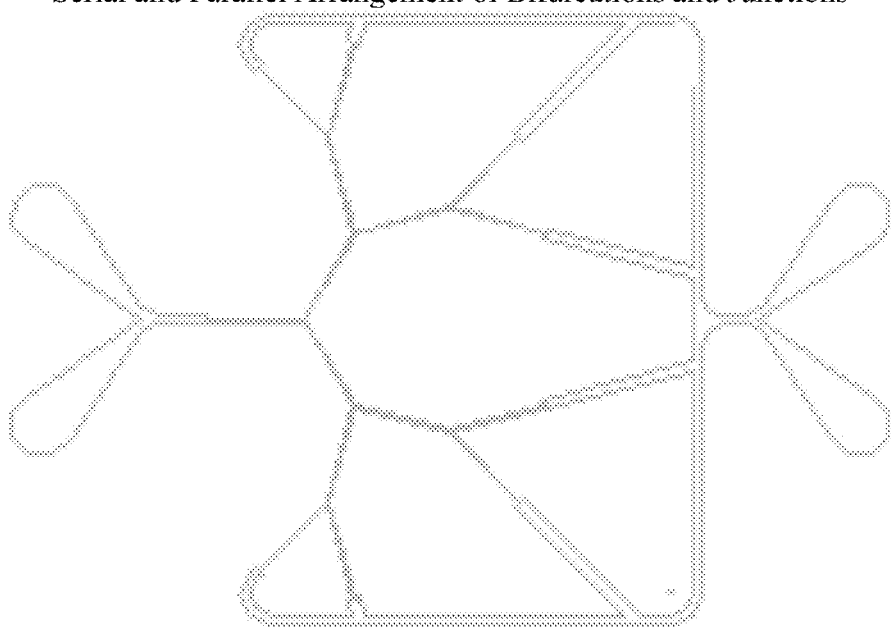
FIG. 15 is a drawing of an idealized microfluidic network comprising a plurality of bifurcations in which no contained angle is repeated and the lengths of the individual branches are maintained constant throughout the network.
Figure 16:
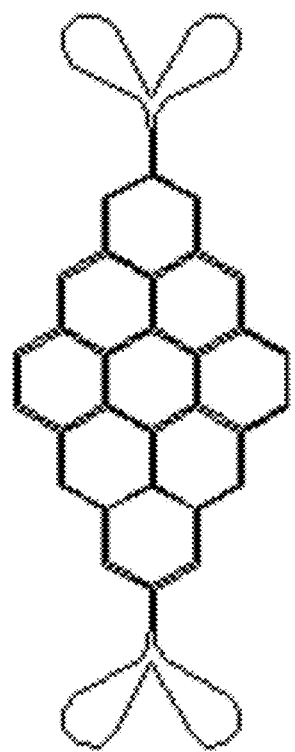
FIG. 16 is a drawing of an idealized microfluidic network comprising a plurality of identical, symmetric bifurcations and junctions.
Figure 17:
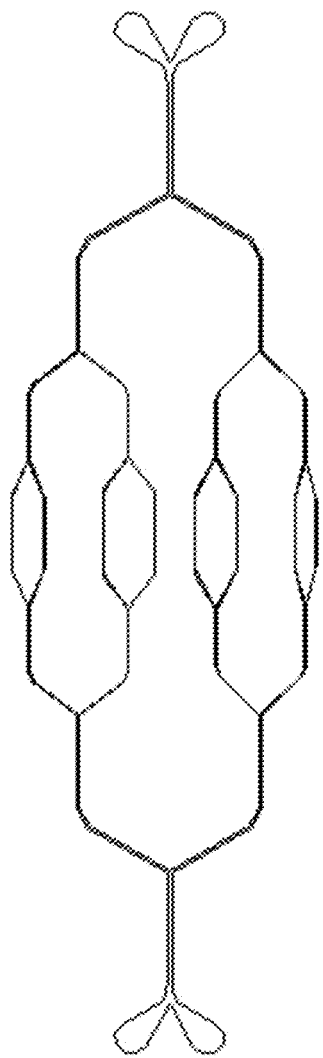
FIG. 17 is a drawing of an idealized microfluidic network comprising a plurality of bifurcations and junctions in which no bifurcation or junction geometry is repeated.

The methods of the present invention may also employ a plurality of idealized bifurcations and junctions arranged to form an idealized microfluidic network. FIG. 15 illustrates a single microfluidic chip comprising a plurality of bifurcations in which no contained angle is repeated and the lengths of the individual branches are maintained constant throughout the network. FIG. 16 illustrates an idealized microfluidic network comprising a plurality of identical, symmetric bifurcations and junctions. FIG. 17 illustrates an idealized microfluidic network comprising a plurality of bifurcations and junctions in which no bifurcation or junction geometry is repeated. The present method may also employ one or a plurality of junctions/bifurcations with more than three channels. Optionally, one or more of the spaces between the channels shown in FIGS. 15-17 can be the tissue spaces as described herein, and the channels can have perforations, holes, pores, or gaps that allow for permeation from the IMN channel into an idealized IMN tissue space.

The IMN can include idealized bifurcations, junctions, and networks of the present invention are preferably made from polydimethylsiloxane (PDMS) using polymeric microfluidic technology but may be made using any one of a variety of techniques commonly used in semiconductor or microfluidic technologies. PDMS offers the advantages of gas permeability beneficial for cell culture, optical transparency, ease of casting, and producing small volume, inexpensive, disposable chips. Very thin (<100 microns) PDMS constructs can be successfully used to for long-term cell culture and cellular assays on microfluidic chips. By bonding the polymer microchannel on to a custom glass bottom laid out in the appropriate form, microfluidic chips may be formed onto standard 24 or 96 well plates, providing for scale-up and high-throughput screening.

The channels forming the bifurcations/junctions may be coated with native or recombinant with proteins, glycoproteins, proteoglycans, or other substrate molecules to assay for associations with particles or to facilitate the growth of cells on the inner surfaces of the channels. Examples of substrate molecules include collagen, gelatin, laminin, and fibronectin. The channels may also be coated with adhesion molecules such as P-selectin, E-selectin, ICAM-1, or other receptors to facilitate adhesion of specific cell types or particles such as liposomes or drug encapsulating or targeting agents. Vascular cells, such as endothelial cells, can also coat the IMN channels.

Microfluidic Chip Fabrication:

Microvascular network structures obtained from in-vivo animal data as for SMN or averaged or idealized microvascular networks (IMN) are patterned onto an optically clear plastic such as PDMS (polydimethylsiloxane) using conventional soft lithography/replica casting techniques and as described in U.S. Ser. No. 11/393,715 to form a SMN. CAD drawings of physiological networks are modified to include gaps in the walls of the vessels. The patterns of these vessels include tissue sections including selected locations ranging from one to the entire tissue space comprising wall sections with gaps with dimensions between 0.2 μm to 5 μm. When fabricated using PDMS, the aspect ratio of these structures should be maintained such that the length (or width) of the structure is greater than twice the channel depth. For 25-50 μm channel depth, this places a minimum requirement on the structure length (and width) of 50-100 μm. The structures are optimally at least 50×50 μm in size. The flow channels may be covered with extracellular matrix components such as fibronectin, collagen, integrins, and other proteins and proteoglycans. Endothelial cells are cultured on the luminal side of the flow channels and tumor cells are cultured in the tissue space(s).

A similar approach is used to fabricate the IMN with gaps with dimensions between 0.2 μm to 5 μm. As before endothelial cells are cultured on the luminal side of the flow channels and tumor cells are cultured in the tissue spaces.

Endothelial cells from any source can be cultured in the vascular channels. Similarly tumor cells from any source, whether adherent or suspension or primary or immortalized, can be cultured in the tumor space. For example, the tumor cells can be immortalized cell lines that are commercially available or primary cells taken directly from a subject. As such, the cells can be cancer cells from a tumor or other cancer cells from a specific subject, such that experiments can be conducted on the specific cancer cells from the specific subject.

Culture of Endothelial Cells and Tumor Cells:

Sterile phosphate buffer saline is injected into a SMN or an IMN at a flow rate of 10 μl/min for 10 minutes using a syringe pump to prime the device. Extracelluar matrix (e.g. fibronectin, gelatin, collagen) at a concentration of 50 μg/ml and flow rate of 10 μl/min is introduced into the chamber for 5 minutes. Flow is stopped and fibronectin solution is allowed to incubate for 2 hrs at room temperature to completely saturate the surfaces. Endothelial cells at a concentration of $5\times10^3$ to $5\times10^7$ cells/ml are introduced into the chamber with media and allowed to incubate for 4 hours. Media is replaced every 24 hours until the cells are confluent (>80%) in the network.

The extracellular tissue spaces are coated with basement membrane matrix such as Matrigel™. (BD Biosciences, Bedford, Mass.). Tumor cells are resuspended at a concentration of $5\times10^3$ to $5\times10^7$ are mixed with Matrigel™ to a final concentration of 0.1 to 1 mg/ml. This mixture is injected into the tissue spaces of the network and allowed to equilibrate in an incubator at 37° C. and 5% $CO_2$ overnight. The microfluidic chip is placed on an automated stage mounted on an inverted microscope equipped with a camera and imaging software.

Adhesion, Transport and Stability Studies of the Delivery Vehicles:

The most important step in delivery of the drug is adhesion of the drug delivery vehicle to the cells in the luminal surfaces followed by transport to the tissue space containing the tumor cells. This adhesion is dependent upon the biochemical component of the delivery vehicle for targeted drug delivery. For example, drug vehicle can be coated with an antibody to molecules such as E-selectin, ICAM-1, P-selectin, RGD, etc. which can bind to endothelial cells on the luminal side. Following this adhesion, the drug delivery vehicle can permeate the pores and transport across to the tumor cells on the tissue side. A common feature attributed to the ineffectiveness of polymer-based delivery vehicles is aggregation in the presence of serum proteins under flow conditions. This aggregation leads to reduced diffusion and ability to deliver drug to the tumor. This procedure provides a non-limiting example of a method for analyzing the stability and transport efficiency of a drug delivery vehicle.

Figure 11:
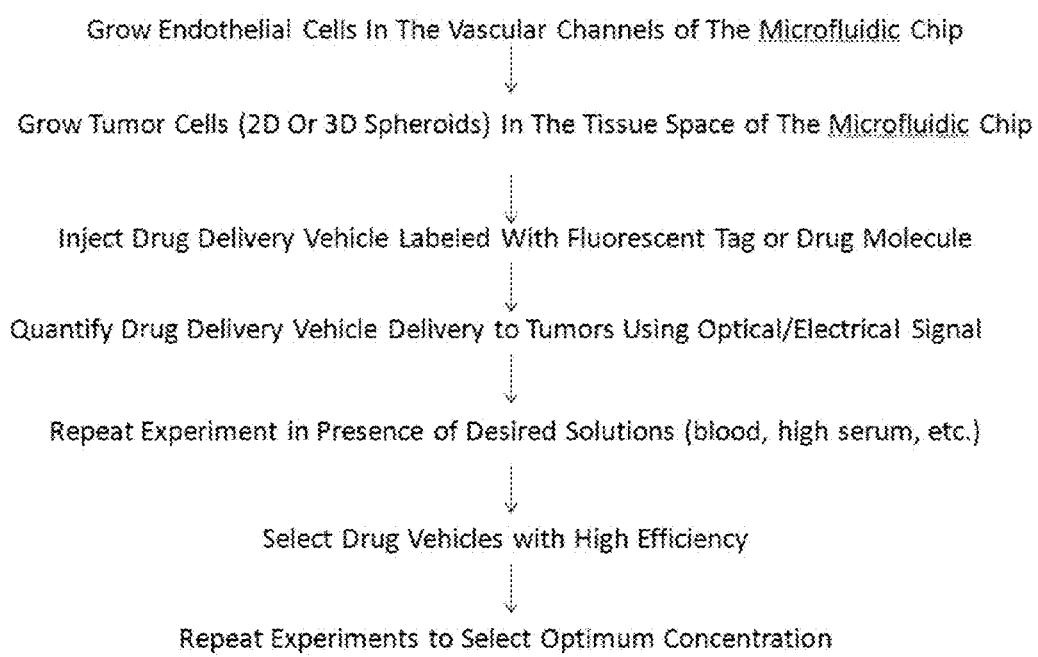
FIG. 11 is a flow chart showing method steps for screening one or more drug delivery vehicles for tumor drug delivery.

Drug delivery vehicles (fluorescently tagged) are introduced into the network inlet at a shear rate at the inlet arm of the network of 500 $sec^{-1}$ using a peristaltic pump or a syringe pump. A range of shear rates from 0-500 $sec^{-1}$ is established in the network and the flow rate is maintained in circulation for 4 hours. Every 30 minutes, the network is scanned to assess the fluorescent intensity in the luminal space and the tissue space of the device. A higher intensity of the drug delivery vehicle indicates maximal transport of the vehicles to the tumor location. Degradation of the delivery vehicles is monitored in the flow channels by analyzing loss of intensity of circulating vehicles and aggregation is monitored by visualization of clumping of delivery vehicles. Concentrations of the delivery vehicles and shear rate are varied to determine the effects of concentration and shear rates on stability, aggregation, and delivery. The experiment is repeated with the drug delivery vehicles suspended in whole blood, apheresed blood, and in media containing white blood cells, red blood cells and/or platelets. FIG. 11 shows general method steps for screening one or more drug delivery vehicles for tumor drug delivery.

Complex flow in the device may be characterized experimentally or using computational fluid dynamics (CFD) simulations in advance of the assay and stored in a database. The experiment may be repeated using flow rates corresponding to different shear rates or the device can be designed to incorporate regions providing different shear rates at the same flow rate at the inlet or inlets to allow data collection at varying shear rates.

Analyzing Gene Delivery by the Delivery Vehicles:

Candidate drug delivery vehicles tagged with a fluorescent protein expression gene are introduced into the inlet of a microfluidic device at shear rate of 500 $sec^{-1}$. A single pass of delivery vehicle is utilized using a syringe pump or they are maintained in circulation using a peristaltic pump for 24 hour. Every 2 hours, the entire network is scanned and stitched to locate the areas of GFP expressing tumor cells. GFP expression is compared with a control lacking the GFP gene as an indicator delivery vehicle success. Similar to the previous assay, concentrations and shear rates can be varied.

Analyzing Drug Delivery by Delivery Vehicles:

A drug coupled to a candidate delivery vehicle is injected into the inlet of the microfluidic device at a shear rate of 500 $sec^{-1}$. Every 2 hours, the entire network is scanned to assess tumor growth in one or more tissue spaces. A reduction in tumor size indicates that the drug is delivered to the tumor.

Tumor growth may be assessed visually and/or electronically. Electrodes may be incorporate into opposing walls of one or more tissue spaces. Tumor cell growth acts as an insulating barrier between the two electrodes. In response to drug delivery to the tissue space, tumor cells die, resulting in a modulation of impedance across the tissue space. Drug delivery vehicles such as nanopolymers, Qdots and other biological or synthetic vehicles can be readily tested.

While the invention is directed primarily toward tumor drug delivery, the methods and apparatus described herein may be altered to assay for drug delivery to other tissues without departing from the spirit of the invention. For example, tissue spaces may contain cells that are not derived from tumors such as non-neoplastic primary cell cultures and cell lines that are transformed to contain recombinant genes. The pore size of porous flow channel walls may also be modified to mimic diffusion across other physiological barriers, including the blood-brain barrier and linings of the small intestine.

Additionally, the devices and methods of the present invention can be combined and applied with the methods and devices of the incorporated references. As such, the methods of the incorporated references, such as particle transport, particle adhesion, leukocyte adhesive cascade, blood-brain barrier diffusion, blood-brain barrier delivery, and the like, can be applied with IMN devices and can be used for studying tumors as described herein.

In one embodiment, an optically transparent microfluidic chip can include: one or more idealized flow channels having one or more inlets and one or more outlets and a first cross-sectional dimension; and one or more tissue spaces bordering the one or more idealized flow channels and having a second cross-sectional dimension, wherein a first wall separating a first idealized flow channel from a first tissue space includes a plurality of apertures that fluidly couple the first idealized flow channel with the first tissue space, the plurality of apertures having a third cross-sectional dimension. In one aspect, the third cross-sectional dimension is smaller than the first cross-sectional dimension and the second cross-sectional dimension is larger than the first cross sectional dimension. In one aspect, the first cross-sectional dimension is from 10 microns to 500 microns, the second cross-sectional dimension is from about 100 microns to 1 cm, and the third cross-sectional dimension is from 0.2 microns to 30 microns. In one aspect, the first cross-sectional dimension can be from about 5 microns to about 500 microns, from about 25 microns to about 250 microns, from about 50 microns to about 150 microns, or about 100 microns. In one aspect, the second cross-sectional dimension can be from about 100 microns to about 1 cm, from about 250 microns to about 5 mm, from about 500 microns to about 2.5 mm, or about 1 mm. In one aspect, the third cross-sectional dimension can be from about 0.2 microns to about 30 microns, from about 0.5 microns to about 15 microns, from about 1 microns to about 5 microns, or about 2 microns.

In one aspect, the one or more idealized flow channels form an idealized microvascular network (IMN). In one aspect, the idealized microvascular network includes one or more idealized flow channels interconnected by one or more idealized bends, junctions, or bifurcations. In one aspect, the one or more idealized bends, junctions or bifurcations include one or more acute, right, or obtuse angles. In one aspect, luminal surfaces of the one or more idealized flow channels of the idealized microvascular network are coated with a first cell type (e.g., endothelial) and the one or more tissue spaces include a different second type of cell (e.g., cancerous). In one aspect, the apertures and/or one or more tissue spaces are filled with a material that is permeable to the second type of cells, wherein the material is selected from a gel, a basement matrix, an extracellular matrix, a tissue matrix, a synthetic matrix, a natural matrix, polymer and combinations thereof.

In one embodiment, the apertures are dimensioned smaller than the first or second types of cell so as to be impermeable thereto. However, the apertures can still be large enough so as to allow the analytes, such as, to pass from the flow channel through the aperture, and into the tissue spaces. Such small pore sizes can range from about 0.5 microns to about 5 microns, or about 1 microns.

In one embodiment, the angles of the one or more idealized bends, junctions or bifurcations range from 15° to 135°. In one aspect, a first bifurcation having a first idealized daughter flow channel with a cross-sectional dimension that is greater than a cross-sectional dimension of a second idealized daughter flow channel of the first bifurcation. In one aspect, a first bifurcation having a first idealized daughter flow channel at an angle that is greater than an angle of a second idealized daughter flow channel of the first bifurcation. In one aspect, a first bifurcation having a first idealized daughter flow channel with a cross-sectional dimension that is greater than a cross-sectional dimension of a second idealized daughter flow channel of the first bifurcation and a first idealized daughter flow channel being at an angle that is greater than an angle of a second idealized daughter flow channel.

In one embodiment, the one or more tissue spaces each include a distinct inlet port configured for introducing fluid and/or cells therein. In one aspect, a valve is in fluid communication with the distinct inlet port of each tissue space, said valve configured to regulate pressure inside the tissue space. In one aspect, each tissue space includes posts configured to promote growth of 3-dimensional tumors. In one aspect, the one or more tissue spaces each include a distinct outlet port.

In one embodiment, luminal surfaces of the one or more idealized flow channels are coated with a substance selected from the group consisting of a protein, a proteoglycan, a chemical moiety, a biomolecule, and combinations thereof.

In one embodiment, the one or more tissue spaces each contain a first type of cell. The flow channels can include a different second type of cell. In one aspect, the one or more tissue spaces may contain one or more of endothelial cells, epithelial cells, fibroblasts, bone marrow cells, embryonic cells, hepatocytes, myocytes, neural cells, adipocytes, first type of cancer cell, second type of cancer cell or normal cells comprising of brain cells, liver cells, heart cells, kidney cells, lung cells, stomach cells, intestine cells, pancreas cells, ovary cells, cervix cells, spleen cells, artery cells, venule cells, capillary cells, connective tissue cells, organ tissue boundary layer cells, connective tissue cells, muscle cells, bone cells, nervous tissue cells, germ cells, stem cells, cultures thereof, 3D tissues thereof, and combinations thereof. The cells can be any type of cell ranging from immortalized cell lines to primary cells to patient-derived cells. In some instance, a tissue culture from a patient can be included. The cell cultures can include a single type of cell or a combination of cells, such as 2, 3, or 4 different types in a co-culture. In some natural tissues, multiple cells may be present, and such tissues can be simulated with a similar cell type combination. Usually, the tissue space can include cancer cells with or without additional types of cells, and the flow channels can include endothelial cells with or without additional types of cells. For example, the flow channels and/or tissue spaces can include cells or cell cultures that simulate the liver, kidney, heart, lung, brain, stomach, intestine, blood brain barrier, vascular networks, or other organs. As such, the flow channels and/or tissue spaces can have unique cell cultures that are indicative of the different cell types or tissue types of an organ, where the cell culture in the flow channels can be different from the cell culture in the tissue space.

The cells can grow only on the bottom, or can grow to confluence on the sides and optionally the top walls of the flow paths and tissue spaces. As such, the cells can grow over the pores of the walls that separate the flow paths from the tissue spaces. Preferably, the cells grow completely around the flow paths and tissue spaces to form a cellular lumen or three-dimensional tissues. Tissue culture scaffold materials can be located in any or all of the tissue spaces as desired. The cells (e.g., endothelial) can grow over the pores on the flow path side but allow analytes or metabolites or other fluid to pass through the pores to an adjacent tissue space. The cells can start growing at the bottom of a flow path or tissue space first, but eventually they fill up the porous side walls and the top walls and all around the flow paths or tissue spaces.

In one embodiment, the one or more tissue spaces are defined by at least two of the idealized flow channels having walls that each include the plurality of apertures that fluidly couple the at least two straight flow channels with the first tissue space. In one aspect, the at least two idealized flow channels each include idealized flow channels connected at bends for form at least two distinct flow channel lumen that define the first tissue space. In one aspect, each wall separating one or more idealized flow channels from the first tissue space include the plurality of apertures that fluidly couple the at least two straight flow channels with the first tissue space.

In one embodiment, a method is provided for assaying a drug delivery vehicle with the IMN. The method includes: providing the optically transparent microfluidic chip of having the one or more idealized flow channels and one or more tissue spaces separated by walls having the plurality of apertures; introducing a liquid containing a drug delivery vehicle and a drug into a first inlet of the one or more idealized flow channels; causing the liquid containing the drug delivery vehicle and the drug to move through the one or more idealized flow channels, through the plurality of apertures, and into the one or more tissue spaces; and quantifying the amount of the drug delivery vehicle and/or a drug reaching the tissue space.

In one embodiment, the method can include providing the optically transparent microfluidic chip that includes luminal surfaces of the one or more idealized flow channels of the idealized microvascular network are coated with a first cell type and the one or more tissue spaces include a different second type of cell; introducing a liquid containing a drug delivery vehicle and a drug into a first inlet of the one or more idealized flow channels; causing the liquid containing the drug delivery vehicle and the drug to move through the one or more idealized flow channels, through the plurality of apertures, and into the one or more tissue spaces; and quantifying the amount of the drug delivery vehicle and/or a drug interacting with the second type of cell.

In one embodiment, the method can include: providing the optically transparent microfluidic chip with one or more tissue spaces each containing a first type of cancer cell; introducing a liquid containing a drug delivery vehicle and a drug into a first inlet of the one or more idealized flow channels; causing the liquid containing the drug delivery vehicle and the drug to move through the one or more idealized flow channels, through the plurality of apertures, and into the one or more tissue spaces; and quantifying the amount of the drug delivery vehicle and/or a drug interacting with the first type of cancer cell.

The method can include one or more of: quantifying the amount of the drug by optical or electrical detection; the drug delivery vehicle is selected from the group consisting of: a cell, a liposome, a lipisome, a lipoprotein, a microencapsulated drug, a particulate drug carrier, a nanoparticle, a microparticle, nanocrystals, a polymer bead, a virus, and a bacterium; the liquid containing the drug delivery vehicle and drug is moved through one or more idealized flow channels once, multiple times, or is recirculated for a desired time or a combination of all using electrokinetic forces, pumps and/or other driving mechanisms; the drug is attached to the drug delivery vehicle and the drug is selected from the group consisting of: a native gene; a recombinant gene a naturally occurring compound, and a synthetic compound; measuring a property of the drug delivery vehicle, said property selected from the group consisting of: realtime circulation, stability, half-life, rate of aggregation, rate of degradation and combinations thereof; moving the liquid with varying fluidic shear rate values of between 1 sec$^{-1}$ and 2000 sec$^{-1}$, or even up to 5000 sec$^{-1}$ or selecting the liquid from the group consisting of: a cell culture media, a buffer containing serum proteins, whole blood, apheresed blood, a buffer containing leukocytes, a buffer containing erythrocytes, and a buffer containing platelets or combinations thereof.

The device can be used to test the effect of any substance on the cells or test ability of the substance to reach the cells in discrete locations in the flow channels or reach the cells in the tissue spaces. The substance can be a biologically active agent that can be any agent that is administered for a function, such as a biological function to improve or otherwise modulate a biological process, such as a biological pathway. However, the agent can be active, such as to emit light, without being biologically active. As such, the biologically active agent can be a traditional pharmaceutical or nutraceutical, and it can be any type of substance for testing or diagnostics. The biologically active agent can be any agent that is administered to a subject in order to elicit a biological response that arises from the biological activity of the agent. The biological response obtained can be a measurable biological response or provide some change that can be analyzed and determined, such as by testing to determine an amount of the biologically active agent to be administered. The biologically active agent can be a toxin or poison or other deleterious substance. Examples can include the biologically active agent being a mineral, vitamin, pharmaceutical, nutraceutical, small molecule, macromolecule, organic molecule, polypeptide, protein, nucleic acid, polynucleotide, derivatives thereof, and combinations thereof. The biologically active agent can be for a human or animal subject. Human and veterinary medicines can be evaluated and improved with the present invention. The substance can be an environmental substance that is natural or manmade and found in the environment. The substance can be a particle. The substance can be a foreign cell not found in an organ, such as a cancer cell, bacteria, yeast, or the like, and even a virus. The test substance can be a particle, such as a micro particle or microsphere.

The test substance can even be a substance commonly used in a pharmaceutical product or combination thereof. The test substance can include the following: a film-forming agent; a filler; a plasticizer; a taste-masking agent; a coloring agent; a solubilizing agent; an effervescent agent; an antioxidant; an absorption enhancer; a disintegrating agent; a pH modifying or buffer agent; a surfactant; a complexing agent; a bioadhesive agent; a sheet adhesive; an identifying agent; an anti-counterfeiting agent; a tracking agent; transporter inhibitor agent; transporter inducer agent; emulsifying agent, self-emulsifying system agents; crystallization inhibitor; crystallization promoter; supersaturation promoting agent; antimicrobial preservative; catalyst; chelating agent; particles; organoleptic agent; flavoring agent; scent agent; identifying device; and/or anti-counterfeiting device.

In one embodiment, cells can be analyzed in any of the flow paths or tissue spaces. However, in some assays, only the cells in the tissue spaces will be assayed. For example, visual analysis, such as with a microscope can be used for analysis of the cells.

In another example, the cells can be identified using optical or electrical methods. For example, cell staining markers specific for cell types can be used. In addition, electrical signals based detection can allow detection of morphology changes (cell differentiation) and different types of cells.

The device may be connected to a flow or pressure regulating system that can regulate the pressure across the flow paths and tissue spaces or within each distinct tissue space. Pumps and valves can be used to regulate the pressure. As such, operation of the device can include regulating the pressures inside each of the flow paths and tissue spaces. For example, a tissue such as liver or the kidney may be leaky, pressure control can be used to simulate such leakiness of the tissue. Also, some tissue like the brain can have very high pressures, which can be simulated with controlling the pumps and valves. The system can regulate the pressure in each of these flow paths and tissue spaces as desired to mimic normal vs. diseased conditions.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety.

This patent document incorporates by specific reference in their entirety the following patents and patent applications: U.S. Ser. No. 11/393,715 now U.S. Pat. No. 7,725,267 (C1478.10001US01); U.S. Ser. No. 12/648,296 now U.S. 2010/0099136 (C1478.10001US02); U.S. Ser. No. 12/428, 134 now U.S. Pat. No. 8,175,814 (C1478.10001US03); U.S. Ser. No. 12/612,573 now U.S. 2010/0112550

(C1478.10001US04); U.S. Ser. No. 12/726,140 now U.S. 2011/0104658 (C1478.10013US01); U.S. Ser. No. 13/332,400 (C1478.10001US05); Ser. No. 12/399,606 now U.S. 2010/0227312 (C1478.10009US01); and 61/730,357 (C1478.10017US01).

The invention claimed is:

1. An optically transparent microfluidic chip comprising:
one or more idealized flow channels having one or more inlets and one or more outlets and a first cross-sectional dimension, each idealized flow channel having one or more linear sections;
one or more tissue spaces bordering the one or more idealized flow channels and having a second cross-sectional dimension; and
two or more connected linear walls of two or more linear sections of a first idealized flow channel, wherein the two or more connected linear walls define two or more connected linear walls of a first tissue space,
wherein a first wall separating the first idealized flow channel from the first tissue space includes a plurality of apertures that fluidly couple the first idealized flow channel with the first tissue space, the plurality of apertures having a third cross-sectional dimension.

2. The microfluidic chip of claim 1, wherein the third cross-sectional dimension is smaller than the first cross-sectional dimension and the second cross-sectional dimension is larger than the first cross sectional dimension.

3. The microfluidic chip of claim 2, wherein the first cross-sectional dimension is from 10 microns to 500 microns, the second cross-sectional dimension is from about 100 microns to 1 cm, and the third cross-sectional dimension is from 0.2 micron to 30 microns.

4. The micro fluidic chip of claim 3, wherein the third cross-sectional dimension is from 0.2 and 5 microns.

5. The microfluidic chip of claim 4, wherein the one or more tissue spaces each include a distinct inlet port configured for introducing fluid and/or cells therein and/or a distinct outlet port.

6. The microfluidic chip of claim 5, further comprising a valve in fluid communication with the distinct inlet port and/or distinct outlet port of each tissue space, said valve configured to regulate pressure inside the tissue space.

7. The microfluidic chip of claim 3, wherein the one or more idealized flow channels form a planar idealized microvascular network that is planar with the one or more tissue spaces.

8. The microfluidic chip of claim 7, wherein the idealized microvascular network includes one or more idealized flow channels interconnected by one or more idealized bends, junctions, or bifurcations, the one or more idealized bends, junctions or bifurcations include one or more acute, right, or obtuse angles.

9. The micro fluidic chip of claim 8, wherein the angles of the one or more idealized bends, junctions or bifurcations range from 15° to 135°.

10. The micro fluidic chip of claim 9, comprising one or more of:
a first bifurcation having a first idealized daughter flow channel with a cross-sectional dimension that is greater than a cross-sectional dimension of a second idealized daughter flow channel of the first bifurcation; or
a first bifurcation having a first idealized daughter flow channel at an angle that is greater than an angle of a second idealized daughter flow channel of the first bifurcation.

11. The micro fluidic chip of claim 9, comprising a first bifurcation having a first idealized daughter flow channel with a cross-sectional dimension that is greater than a cross-sectional dimension of a second idealized daughter flow channel of the first bifurcation and a first idealized daughter flow channel being at an angle that is greater than an angle of a second idealized daughter flow channel.

12. The microfluidic chip of claim 8, wherein luminal surfaces of the one or more idealized flow channels of the idealized microvascular network are coated with a first cell type and the one or more tissue spaces include a different second type of cell.

13. The microfluidic chip of claim 12, wherein the apertures and/or one or more tissue spaces are filled with a material that is permeable to the second type of cells, wherein the material is selected from a gel, a basement matrix, an extracellular matrix, a tissue matrix, a synthetic matrix, a natural matrix, polymer and combinations thereof.

14. The micro fluidic chip of claim 12, wherein the first cell type includes endothelial cells and the second cell type includes cancer cells.

15. The microfluidic chip of claim 14, wherein each tissue space includes posts configured to promote growth of 3-dimensional tumors.

16. The microfluidic chip of claim 12, wherein the apertures and/or one or more tissue spaces are filled with a material that is impermeable to the first and second types of cells, but is permeable to analytes, wherein the material is selected from selected from a gel, a basement matrix, an extracellular matrix, a tissue matrix, a synthetic matrix, a natural matrix, polymer and combinations thereof.

17. The microfluidic chip of claim 12, wherein the apertures are dimensioned smaller than the first or second types of cell so as to be impermeable thereto.

18. The microfluidic chips of claim 12, wherein the first type of cell includes endothelial cells and the second type of cell includes cancer cells, and the one or more tissue spaces contain a third type of cell.

19. The microfluidic chip of claim 1, wherein luminal surfaces of the one or more idealized flow channels are coated with a substance selected from the group consisting of a protein, a proteoglycan, a chemical moiety, a biomolecule, and combinations thereof.

20. The microfluidic chip of claim 1, wherein the one or more tissue spaces each have a shape that is defined by at least two of the idealized flow channels having the walls that each include the plurality of apertures that fluidly couple the at least two idealized flow channels with the first tissue space.

21. The microfluidic chip of claim 20, wherein the at least two idealized flow channels each include two or more linear sections connected at bends to define the shape of the first tissue space.

22. The microfluidic chip of claim 1, wherein each wall separating the one or more idealized flow channels from the first tissue space includes the plurality of apertures that fluidly couple the one or more at least two straight flow channels with the first tissue space.

23. The microfluidic chip of claim 1, wherein the one or more idealized flow channels surround the one or more tissue spaces.

24. The microfluidic chip of claim 1, wherein the one or more idealized flow channels define a perimeter the one or more tissue spaces.

25. A method for assaying a drug delivery vehicle comprising the steps of:
providing the optically transparent microfluidic chip of claim 1;

introducing a liquid containing a drug delivery vehicle and a drug into a first inlet of the one or more idealized flow channels;

causing the liquid containing the drug delivery vehicle and the drug to move through the one or more idealized flow channels, through the plurality of apertures, and into the one or more tissue spaces; and quantifying the amount of the drug delivery vehicle and/or a drug reaching the one or more tissue spaces.

26. The method of claim 25, comprising one or more of:

quantifying the amount of the drug by optical or electrical detection;

the drug delivery vehicle is selected from the group consisting of: a cell, a liposome, a lipisome, a lipoprotein, a microencapsulated drug, a particulate drug carrier, a nanoparticle, a microparticle, nanocrystals, a polymer bead, a virus, and a bacterium;

the liquid containing the drug delivery vehicle and drug is moved through one or more idealized flow channels once, multiple times, or is recirculated for a desired time or a combination of all using electrokinetic forces, pumps and/or other driving mechanisms;

the drug is attached to the drug delivery vehicle and the drug is selected from the group consisting of: a native gene; a recombinant gene, a naturally occurring compound, and a synthetic compound;

measuring a property of the drug delivery vehicle, said property selected from the group consisting of: real-time circulation, stability, half-life, rate of aggregation, rate of degradation, amount of adhesion, rate of adhesion, and combinations thereof;

moving the liquid with varying fluidic shear rate values of between 1 $sec^{-1}$ and 5000 $sec^{-1}$; or selecting the liquid from the group consisting of: a cell culture media, a buffer containing serum proteins, whole blood, apheresed blood, a buffer containing leukocytes, a buffer containing erythrocytes, and a buffer containing platelets or combinations thereof.

27. A method for assaying a drug delivery vehicle comprising the steps of:

providing the optically transparent micro fluidic chip of claim 12;

introducing a liquid containing a drug delivery vehicle and a drug into a first inlet of the one or more idealized flow channels;

causing the liquid containing the drug delivery vehicle and the drug to move through the one or more idealized flow channels, through the plurality of apertures, and into the one or more tissue spaces; and quantifying the amount of the drug delivery vehicle and/or a drug interacting with the second type of cell.

28. The method of claim 27, comprising one or more of:

quantifying the amount of the drug by optical or electrical detection;

the drug delivery vehicle is selected from the group consisting of: a cell, a liposome, a lipisome, a lipoprotein, a microencapsulated drug, a particulate drug carrier, a nanoparticle, a microparticle, nanocrystals, a polymer bead, a virus, and a bacterium;

the liquid containing the drug delivery vehicle and drug is moved through one or more idealized flow channels once, multiple times, or is recirculated for a desired time or a combination of all using electrokinetic forces, pumps and/or other driving mechanisms;

the drug is attached to the drug delivery vehicle and the drug is selected from the group consisting of: a native gene; a recombinant gene a naturally occurring compound, and a synthetic compound;

measuring a property of the drug delivery vehicle, said property selected from the group consisting of: real-time circulation, stability, half-life, rate of aggregation, rate of degradation, amount of adhesion, rate of adhesion, and combinations thereof;

moving the liquid with varying fluidic shear rate values of between 1 $sec^{-1}$ and 5000 $sec^{-1}$; or selecting the liquid from the group consisting of: a cell culture media, a buffer containing serum proteins, whole blood, apheresed blood, a buffer containing leukocytes, a buffer containing erythrocytes, and a buffer containing platelets or combinations thereof.

29. The method of claim 27, wherein the drug delivery vehicle binds to a first idealized flow channel and/or first cell type coated thereon and then moves into a first tissue space through at least one aperture fluidly coupling the first idealized flow channel and first tissue space.

30. A method for assaying a drug delivery vehicle comprising the steps of:

providing the optically transparent micro fluidic chip of claim 18;

introducing a liquid containing a drug delivery vehicle and a drug into a first inlet of the one or more idealized flow channels;

causing the liquid containing the drug delivery vehicle and the drug to move through the one or more idealized flow channels, through the plurality of apertures, and into the one or more tissue spaces; and quantifying the amount of the drug delivery vehicle and/or drug interacting with the cells in the luminal spaces followed by quantifying the amount of the drug delivery vehicle and/or a drug interacting with cells in the one or more tissue spaces.

31. The method of claim 30, comprising one or more of:

quantifying the amount of the drug by optical or electrical detection;

the drug delivery vehicle is selected from the group consisting of: a cell, a liposome, a lipisome, a lipoprotein, a microencapsulated drug, a particulate drug carrier, a nanoparticle, a microparticle, nanocrystals, a polymer bead, a virus, and a bacterium;

the liquid containing the drug delivery vehicle and drug is moved through one or more idealized flow channels once, multiple times, or is recirculated for a desired time or a combination of all using electrokinetic forces, pumps and/or other driving mechanisms;

the drug is attached to the drug delivery vehicle and the drug is selected from the group consisting of: a native gene; a recombinant gene a naturally occurring compound, and a synthetic compound;

measuring a property of the drug delivery vehicle, said property selected from the group consisting of: real-time circulation, stability, half-life, rate of aggregation, rate of degradation, amount of adhesion, rate of adhesion, and combinations thereof;

moving the liquid with varying fluidic shear rate values of between 1 $sec^{-1}$ and 5000 $sec^{-1}$; or selecting the liquid from the group consisting of: a cell culture media, a buffer containing serum proteins, whole blood, apheresed blood, a buffer containing leukocytes, a buffer containing erythrocytes, and a buffer containing platelets or combinations thereof.

* * * * *